(12) United States Patent  
Carr

(10) Patent No.: US 7,989,741 B2
(45) Date of Patent: Aug. 2, 2011

(54) IN-LINE MICROWAVE WARMING APPARATUS

(75) Inventor: Kenneth L. Carr, Woolwich, ME (US)

(73) Assignee: Meridian Medical Systems, LLC, Woolwich, ME (US)

( * ) Notice: Subject to any disclaimer, the term of this patent is extended or adjusted under 35 U.S.C. 154(b) by 1120 days.

(21) Appl. No.: 11/745,507

(22) Filed: May 8, 2007

(65) Prior Publication Data

US 2008/0277388 A1    Nov. 13, 2008

(51) Int. Cl.
    H05B 6/64    (2006.01)
    H05B 6/72    (2006.01)
    A61F 2/00    (2006.01)

(52) U.S. Cl. .................... 219/693; 219/761; 607/101

(58) Field of Classification Search .......... 219/678, 219/679, 687–696, 702, 710–713; 604/114; 607/90, 98–106

See application file for complete search history.

(56) References Cited

U.S. PATENT DOCUMENTS

| 5,073,167 A | 12/1991 | Carr et al. |
| 5,683,381 A | 11/1997 | Carr et al. |
| 5,690,614 A | 11/1997 | Carr et al. |
| 5,782,897 A | 7/1998 | Carr |
| 5,919,218 A | 7/1999 | Carr |
| 6,932,776 B2 | 8/2005 | Carr |

*Primary Examiner* — Quang T Van

(74) *Attorney, Agent, or Firm* — Cesari and McKenna, LLP; John F. McKenna

(57) ABSTRACT

Microwave warming apparatus includes a housing defining a heating waveguide with a heating cavity. An integral internal electrically conductive ridge projects from one of the longitudinal waveguide walls and extends along the waveguide. A slot having opposite ends extends from the outside through the ridge into the heating cavity, the slot being adapted to receive a cartridge containing a tube so that the tube extends through the slot into the heating cavity. Electromagnetic energy is coupled into the heating waveguide to heat the contents of the tube. A transducer constituted by a first receiving waveguide inside the ridge is adjacent to the slot so that when a cartridge is received in the slot, the transducer can sense the thermal radiation emanating from a segment of the tube and produce a corresponding waveguide-generated signal. A radiometer in the housing is responsive to the waveguide-generated signal and produces a temperature indicating signal.

18 Claims, 5 Drawing Sheets

IN-LINE MICROWAVE WARMING APPARATUS

BACKGROUND OF THE INVENTION

1. Field of the Invention

This invention relates to in-line microwave warming apparatus for warming blood and other fluids.

2. Background Information

In many applications, particularly in the medical field, there may be a requirement that a circulating fluid be warmed. For example, in cardiac surgery during extra-corporeal circulation (ECC), the patient is first cooled in order to slow metabolism and thereafter the circulating blood is warmed to return it to body temperature. As another example, heated intravenous fluids are useful in hypothermic patients and in trauma patients requiring massive IV resuscitation.

Microwave energy has, in the past, been used in connection with the heating of blood and intravenous fluids. For example, my U.S. Pat. Nos. 5,073,167 and 5,919,218, whose entire contents are incorporated herein by reference, disclose microwave apparatus comprising a waveguide heating cavity having a source of microwave energy coupled thereto. A support element encircled by a fixed length of tubing forms a disposable cartridge which may be positioned in the heating cavity. The characteristics, and placement within the heating cavity, of the cartridge are such that there results a rapid, uniform heating of the fluid flowing through the cartridge.

Such prior apparatus also includes means for non-invasively monitoring the temperature of fluid flowing through the cartridge and thereby controlling the energy source so as to maintain the flowing fluid at a selected temperature. These means include an external fluid inlet temperature transducer and an external fluid outlet temperature transducer. Since these transducers are external to the heating cavity, a third transducer is needed to measure the temperature of the fluid within the cavity. This is necessary to address the situation wherein the fluid flow is suddenly stopped for some reason and the output transducer is calling for heat because it senses a temperature drop. In other words, the fluid could severely overheat before the outlet transducer recognizes the problem. Resultantly, when flow resumes, the overheated fluid could injure the patient.

While the above-described patented in-line microwave warmers provide distinct advantages over the prior water immersion-type warmers, they have certain drawbacks which may limit their use and application. For example, as noted above, they require three separate temperature monitors each of which consists of a transducer and a radiometer. Also, the cartridges in the patented apparatus require multiple turns of tubing in order to achieve the desired warming effect. Such a multi-turn tubing cartridge is quite large and has a relatively large priming volume, in the order or 4 ml. In addition, the large cartridge necessitates a commensurately large opening in the heating cavity in order to receive the cartridge. This means that steps must be taken to ensure that microwave radiation does not leak from the heating cavity at that opening. For example, the patented cartridge is provided with a complex metal ground plane to inhibit such radiation leakage.

Still further, in the prior apparatus reflected in the above patents, the transducer in the heating cavity receives signals from all of the windings in the cartridge and accordingly senses the average temperature of the fluid in the multiple windings rather than the temperature of the fluid just as the fluid exits the heating cavity.

Still further, the two external transducers, three separate external radiometers and the multiple cables connecting the various temperature transducers to the radiometers, increase the overall complexity and footprint of the prior apparatus.

SUMMARY OF THE INVENTION

Accordingly, it is an object of the present invention to provide in-line microwave warming apparatus having dramatically reduced complexity and parts count which, in turn, minimizes the cost of the apparatus.

Another object of the invention is to provide in-line microwave warming apparatus whose cartridge is small enough to be received in a thin opening into the heating cavity so that minimal radiation can enter or leave the cavity via that opening.

Yet another object of the invention is to provide apparatus of this type whose cartridge consists of a single tubing turn having a minimal priming volume.

A further object of the invention is to provide in-line microwave warming apparatus which requires only two temperature monitors both of which are inside the apparatus so that external transducers, radiometers and cables thereto are not required.

Another object of the invention is to provide in-line microwave warming apparatus of this type which is relatively easy to make and to operate.

Other objects will, in part, be obvious and will, in part, appear hereinafter. The invention according comprises the features of construction, a combination of elements and arrangement of parts which will be exemplified in the following detailed description, and the scope of the invention will be indicated in the claims.

Briefly, my apparatus comprises a three-dimensional waveguide which defines a heating cavity. Microwave energy from a microwave transmitter is coupled to the waveguide at a location spaced longitudinally from the heating cavity as described in my above patents. An opening in a form of a thin slot is provided in one of the walls of the waveguide at the heating cavity to accommodate a cartridge.

In this case, however, the cartridge comprises a single turn or loop of tubing whose opposite ends are terminated by connectors. The tubing turn is supported and shaped by a flat, dielectric support member so that the tubing turn has opposite legs which are straight, coplanar and spaced apart a selected distance as will be described later. The cartridge is arranged to be slid into the slot in the waveguide so that the tube legs extend perpendicular to the longitudinal axis of the waveguide at the heating cavity. When the cartridge is so seated in the heating cavity, the slot and cartridge are sufficiently thin or narrow as to prevent leakage of radiation to or from the heating cavity.

An internal longitudinal conductive ridge projects from the waveguide wall containing the slot. This ridge is aligned with the slot and may extend the entire length of the waveguide. Thus, the slot passes through the ridge into the heating cavity. Also, segments of the ridge comprise, with the cartridge support member, a pair of receiving waveguides that form internal transducers for detecting thermal radiation from fluid in the cartridge tube just as the fluid enters and leaves the heating cavity.

These waveguide-detected signals are led out of the heating cavity via waveguide-to-MIC conductor transitions which are part of a printed circuit present inside the apparatus. That circuit includes a radiometer and a switch which connects the transitions alternatively to the radiometer so that the same radiometer can provide both fluid inlet and outlet temperature signals. These signals are then used to control a display. The radiometer signals may also be employed to control the heating transmitter to change the warming characteristics of the apparatus.

BRIEF DESCRIPTION OF THE DRAWINGS

For a fuller understanding of the nature and objects of the invention, reference should be made to the following detailed description taken in connection with the accompanying drawings, in which.

DETAILED DESCRIPTION OF AN ILLUSTRATIVE EMBODIMENT

Figure 1:
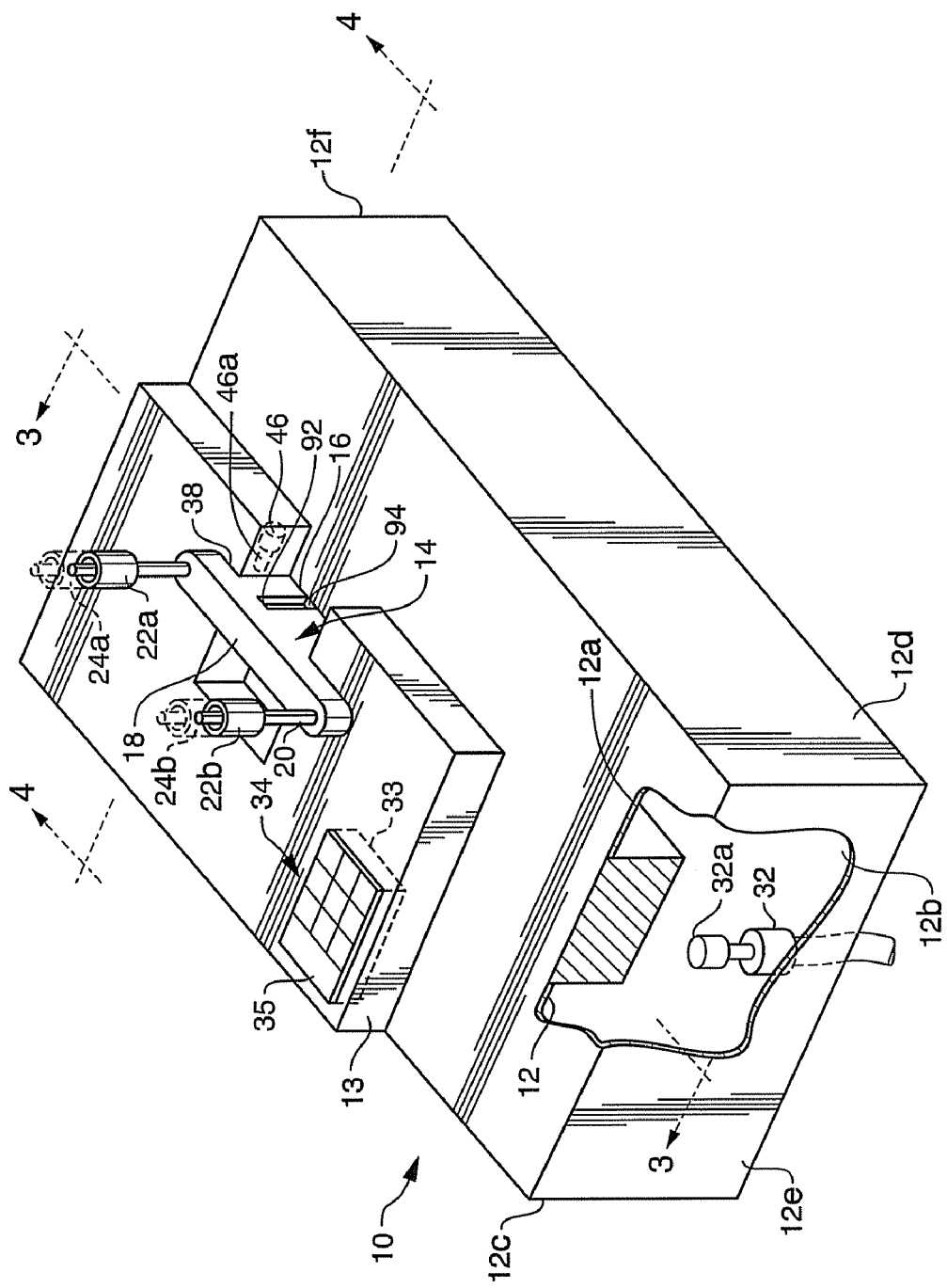
FIG. 1 is an isometric view, with parts cut away, showing in-line microwave warming apparatus incorporating the invention.

Referring to FIG. 1 of the drawings, my apparatus comprises a housing shown generally at 10 which defines a longitudinally extending waveguide 12 with a C-shaped promontory 13 atop the waveguide. The apparatus also includes a cartridge indicated generally at 14 which may be received in a slot 16 in housing 10 so that the cartridge protrudes through the arms of promontory 13 into the waveguide 12.

Cartridge 14 comprises a support member 18 which supports a length of tubing 20 whose opposite ends are terminated by conventional connectors 22a and 22b. Connector 22a, usually a female connector, may be connected to a mating connector 24a at the end of tubing leading to a source of fluid such as a blood bag or fluid administration set (not shown). Connector 22b, usually a male connector, may be connected to a mating connector 24b at the end of tubing leading to a fluid destination such as a catheter (not shown). As is evident from FIG. 1, the waveguide 12 has a pair of relatively broad upper and lower walls 12a and 12b, respectively, a pair of narrower side walls 12c and 12d, respectively, and a pair of end walls 12e and 12f, respectively. The waveguide is thus a three-dimensional body having a width (X direction), a height (Y direction) and a length (Z direction) which defines a heating cavity 12' (FIG. 3) within the waveguide. The slot 16 opens into cavity 12' and the cartridge 14, including its tube 20, projects through the slot into that cavity.

At the heating cavity 12' of the waveguide, fluid flowing through tube 20 is heated by energy from a microwave transmitter (not shown) coupled into the waveguide 12 by means of a coaxial-to-waveguide connector 32 mounted in the bottom wall 12b of housing 10 at a location spaced along the waveguide 12, i.e. in the Z direction, from the heating cavity 12'.

The connector 32, which may be a standard type N connector, has a probe 32' which projects into waveguide 12 and functions as an antenna to conduct electromagnetic energy (TEM) from the connector into the waveguide so that the energy propagates in a $TE_{10}$ mode for the particular dimensions of the waveguide. While these dimensions may vary, the illustrated waveguide 12 may be 3.40 inches wide and 1.65 inches high. For a microwave transmitter operating at a frequency of 2.45 GHz, these dimensions place the frequency of operation in an ideal location in the frequency spectrum. That is, the frequency is sufficiently far enough from the cut-off frequency (1.37 GHz) so that minimum attenuation is obtained for the $TE_{10}$ mode of propagation and yet higher order modes are cut-off.

Of course, instead of a coaxial-to-waveguide transition between the microwave transmitter and the apparatus 10, a suitable feed waveguide (not shown) may extend from the transmitter to housing 10.

In order to couple the maximum amount of energy into the waveguide 12, the connector 32 (or feed waveguide) should be positioned from the adjacent end wall 12e of waveguide 12 a distance equal to one quarter wavelength or multiple thereof at the transmitter frequency, as described in the above patents. The microwave energy coupled to the heating cavity 12' of waveguide 12 warms the fluid flowing through cartridge 14 quite efficiently.

In a manner described in the above patents, the illustrated apparatus monitors the temperature of the fluid flowing through cartridge 14 at the heating cavity 12' and uses that information to regulate the microwave energy coupled into the waveguide 12. In this way, the temperature of the fluid leaving cartridge 14 may be maintained at a selected value independently of the fluid flow rate and the fluid inlet temperature.

The operation of apparatus 10 is controlled by a controller 33 mounted in the apparatus, e.g. in promontory 13. Control settings, e.g. desired temperature, warming time, etc., may be set into the controller 33 via a keypad 34 exposed in the housing at the upper surface of the promontory and relevant data may be displayed by an LCD display 35 positioned next to the keypad and controlled by controller 33.

Figure 2:
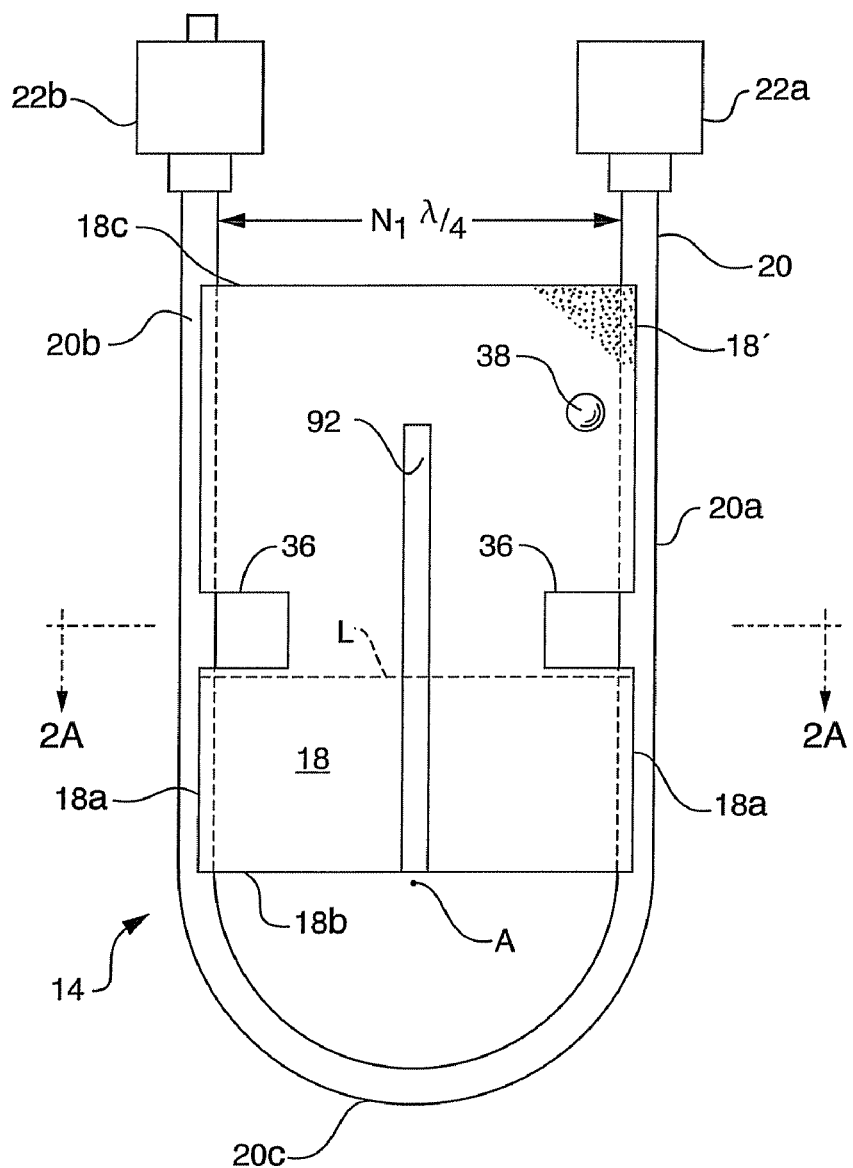
FIG. 2 is a front elevational view of the cartridge component of the FIG. 1 apparatus.
Figure 2A:
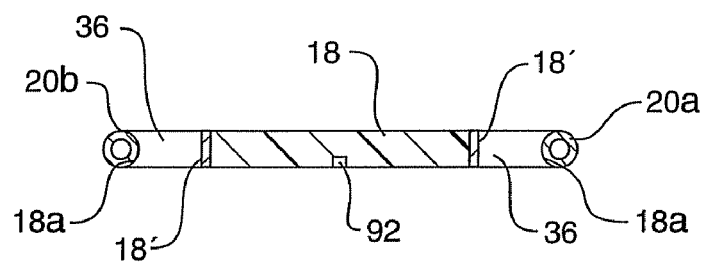
FIG. 2A is a sectional view taken along line 2A-2A of FIG. 2.

Refer now to FIGS. 2 and 2A which show the cartridge 14 in greater detail. It is preferably a disposable item comprising a single turn or loop of the plastic tubing 20 which is wrapped around and supported by support member 18. Preferably, tube 20 is relatively short, e.g. 9.0 inches and has a relatively small internal diameter, e.g. 0.131 inch, so that cavity 14 has a small flow priming volume, i.e. less than 1.0 ml, yet still allows unrestricted fluid flow through the apparatus. Member 18 consists of a flat plate whose opposite side walls 18a, 18a are straight, parallel and concave to bed the two legs or segments 20a and 20b of tube 20 so that those legs are straight, parallel and coplanar. The tube segments 20a, 20b may be secured to support member 18 by a suitable adhesive or by RF welding. The bridging segment 20c of tube 20 that extends between the tube legs 20a, and 20b is more or less a semi-circle having an axis A located at or adjacent to the lower end 18b of support member 18.

Figure 5:
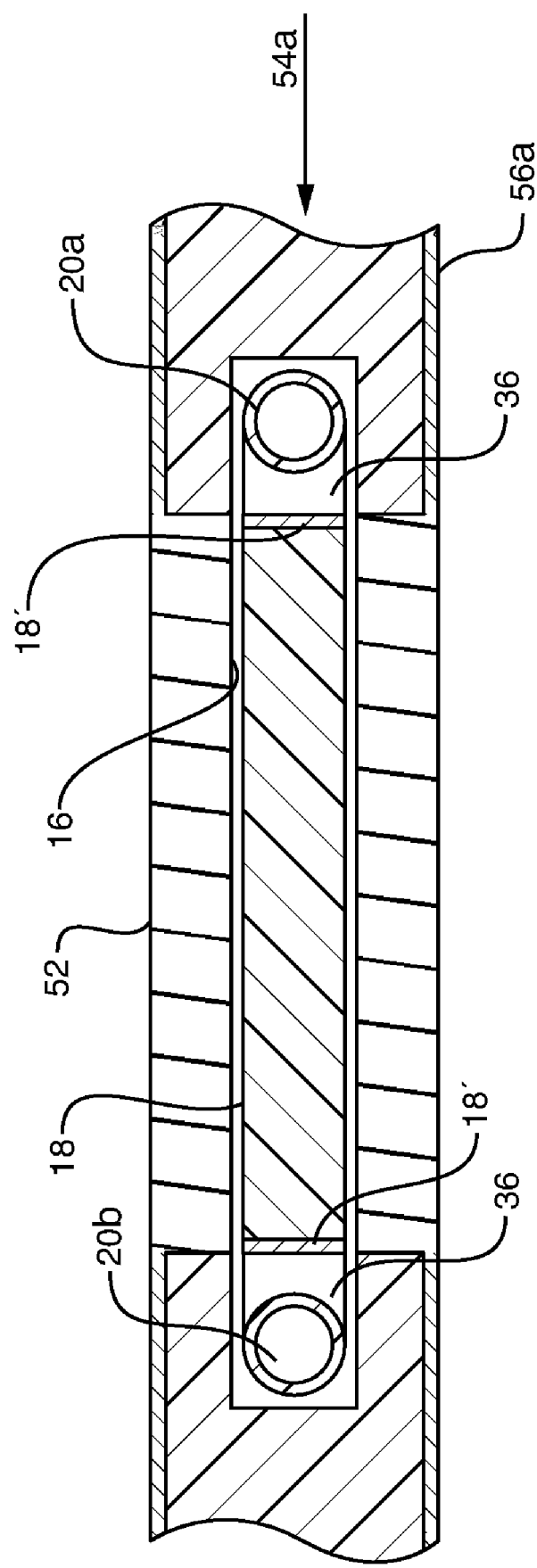
FIG. 5 is a fragmentary sectional view on a larger scale taken along line 5-5 of FIG. 4.

For reasons that will be described later, the support member 18 has a pair of opposed notches 36 extending in from the side edges 18a, 18a of the support member. These notches are positioned so that when cartridge 14 is inserted into housing 10, they coact with the structure therein to help form a pair of transducers $T_I$ and $T_O$ (FIG. 3) that sense the temperature of the fluid flowing into and out of the cartridge 14. The support member 18 is molded of a lightweight, relatively rigid dielectric material such as polystyrene and has metallized surfaces 18' at the walls of notches 36 as best seen in FIGS. 2, 2A and 5 so that those walls are electrically conductive. The upper edge margin of member 18, i.e. above line L in FIG. 2, may also have a conductive metal coating 18' all around for reasons that will be described later. Suffice it to say here that this is the margin of support 18 that lies above cavity 12' when cartridge 14 is seated in housing 10.

Preferably, the width of the support member 18 should be such that the spacing of the two tube legs 20a, 20b is substantially equal to a quarter wavelength or multiple thereof at the operating frequency of the transmitter, i.e. $N_1 \lambda_T/4$. This spacing, which is about 1.8 inches for the illustrated cartridge 14, provides a matched load at the aforesaid heating frequency. Preferably also, the support member 18 should be formed with a dimple or detent 38 near an upper corner thereof. As will be described later, the dimple helps to releasably retain cartridge 14 at its seated position in slot 16 of housing 10 and contributes to an interlock.

Figure 3:
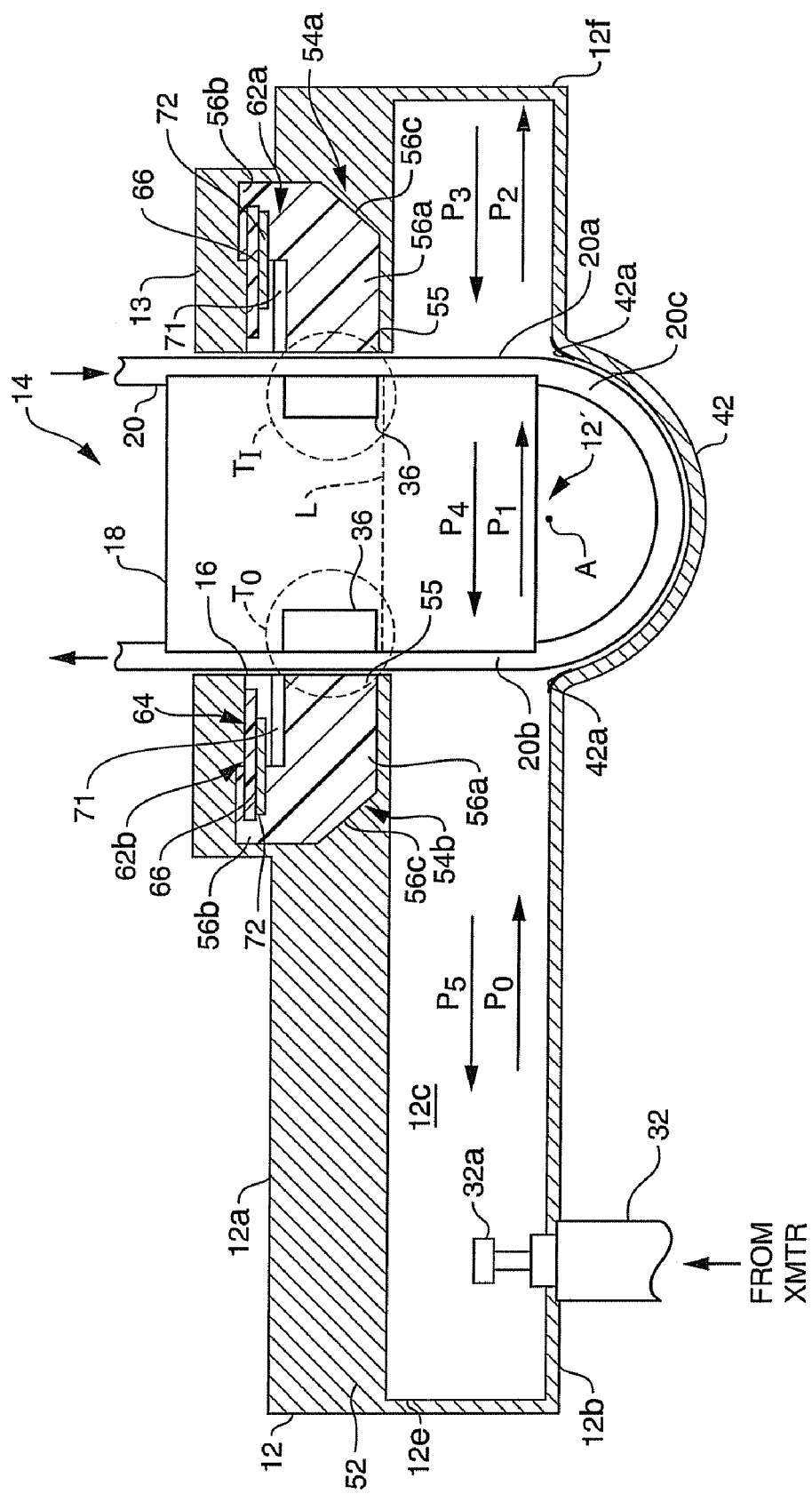
FIG. 3 is a sectional view, with parts shown in elevation, taken along line 3-3 of FIG. 1.
Figure 4:
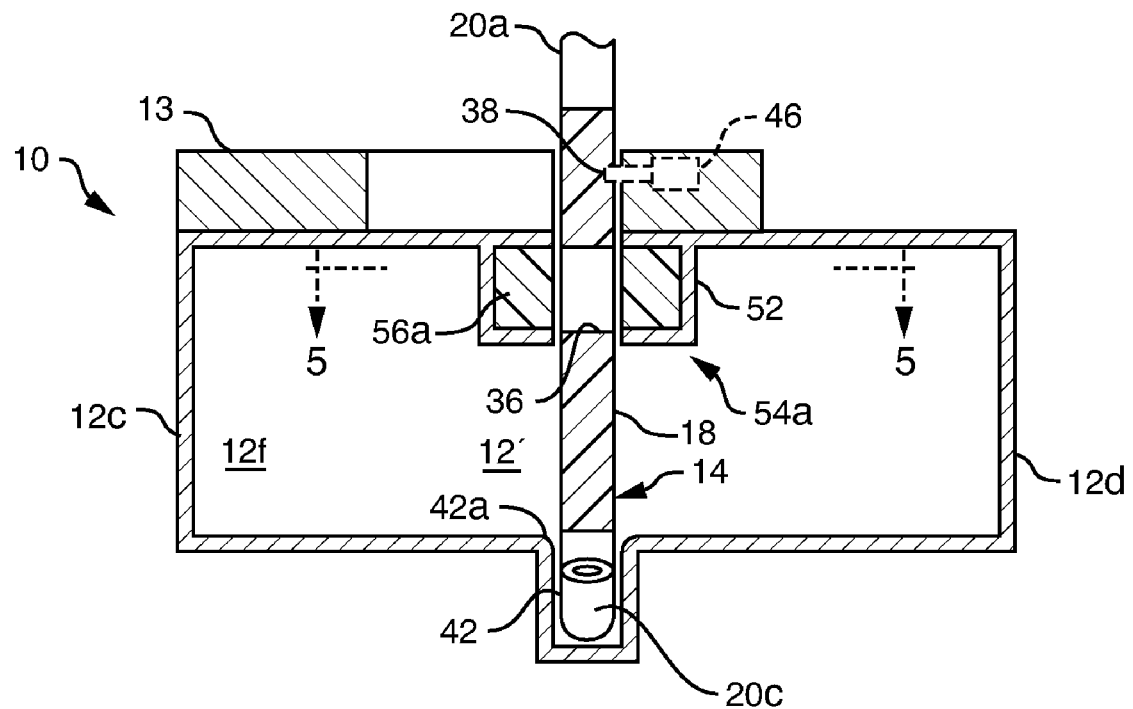
FIG. 4 is a sectional view taken along line 4-4 of FIG. 1.
Figure 6:
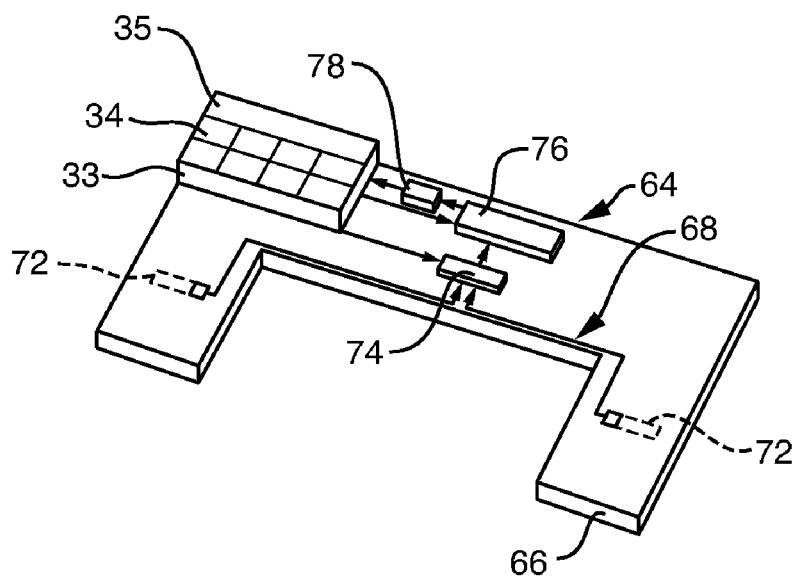
FIG. 6 is a diagrammatic view showing a portion of the FIG. 1 apparatus in greater detail.

Refer now to FIGS. 3 and 4, the bottom wall of 12b of waveguide 12 is formed with a narrow recess 42 which is positioned at the longitudinal axis (Z) of waveguide 12 directly opposite the slot 16 in housing 10. Recess 42 is shaped and arranged to snugly receive the segment 20c of the cartridge tube 20. Preferably, the outside corners 42a at the entrance to recess 42 are rounded or flared to help guide the lower end of cartridge 14 into recess 42 so that the cartridge will seat properly in the waveguide cavity 12'.

Recess 42 is dimensioned so that when the cartridge is seated, the axis A of tube segment 20c will be located at or just below the plane defined by edges 42a. This assures that only the straight segments or legs 20a, 20b of that tube will be located in the heating cavity 12' of waveguide 12. On the other hand, the curved segment 20c of the tube in recess 42 is essentially embedded in the waveguide bottom wall 12b. Accordingly, that segment and its fluid contents have essentially no effect on the power attenuation characteristics of the apparatus.

Preferably, for maximum heating efficiency, the cartridge 14 is positioned in housing 10 so that the legs 20a and 20b are spaced from the adjacent waveguide end walls 12e and 12f, respectively, a distance equal to an integral multiple of a quarter wavelength at the heating frequency.

Thus, cartridge 14 may be inserted into the slot in housing 10 much like a credit card. When the cartridge is properly seated in the waveguide 12 as shown in FIG. 1, the spring-loaded plunger 46a of a microswitch 46 located in promontory 13 adjacent to slot 16 engages in the dimple 38 in the cartridge support member 18. This engagement serves not only to releasably retain the cartridge in housing 10, it also results in an enabling signal being sent to controller 33 so that the apparatus is operative only when the cartridge is properly seated in the housing.

Still referring to FIGS. 3 and 4, in accordance with the invention, waveguide 12 is formed with an internal conductive ridge or ridge guide 52 extending down from the waveguide top wall 12a at the longitudinal centerline of that wall. Ridge 52 has a generally rectangular cross-section being, for example, 0.45 inches high and twice as wide (inside dimension). It may extend the entire length of the waveguide 12 as shown or it may stop short of probe 32a. Also, while the illustrated ridge 52 is located entirely within the waveguide 12, it could extend up through waveguide wall 12a to some extent. That being the case, slot 16 passes through the ridge into heating cavity 12'. Ridge 52 forms a high pass filter with a pass band of 3.75 to 4.2 GHz which is the temperature measuring or detection frequency band. The fact that the illustrated ridge extends the full length of the waveguide 12 assures a broad-band impedance match at the heating frequency. As we shall see, segments of ridge 52 opposite the ends of slot 16 consititute a pair of receiving waveguides that form the above-mentioned transducers $T_I$ and $T_O$ which monitor the temperature of the fluid entering and leaving the cartridge 14 in the heating cavity 12'.

When the apparatus is in operation, microwave energy is emitted from probe 32a as shown in FIG. 3. As seen there, $P_0$ represents the applied power and the power attenuation is as follows:

$P_1$=$P_0$ less the power absorbed by fluid in the tube leg 20b,
$P_2$=$P_1$ less the power absorbed by fluid in the tube leg 20a,
$P_3$=Power reflected at wall 12f constituting the waveguide back plate,
$P_3$=$P_2$,
$P_4$=$P_3$ less the power absorbed by fluid in the tube leg 20a,
$P_4$=$P_3$ less the power absorbed by fluid in fluid leg 20b, and
$P_5$=the remaining power not absorbed, or $P_4$ less the power absorbed by fluid in tube leg 20b.

As an example, an applied power of 100 watts and a single pass loss per fluid column in legs 20a, 20b of 3 dB would result in a total power absorbed of 93.7 watts. This is equivalent to 93.7% power absorbed and a return loss of approximately of 12 dB. Thus, the power absorbed by the fluid in tube 20 at heating cavity 12' is sufficient to heat that fluid to a desired temperature as the fluid flows through cartridge 14. The heating pattern produced by the waveguide 12 is evenly distributed between the tube inlet and outlet legs 20a and 20b. Half the power is absorbed in the initial pass and the remaining power which is reflected from waveguide wall 12f is absorbed by the fluid on the return pass so that the heating efficiency of the apparatus is quite high.

As shown in FIGS. 3 and 4, in accordance with the invention, segments of the conductive ridge 52 opposite the ends of slot 16 are hollowed out to help form a pair of mirror-image receiving waveguides 54a and 54b. Preferably, the waveguides 54a and 54b are filled with a dielectric material 55 (e.g. K=4.5) so that the two waveguides can be relatively small yet provide a proper impedance match at the desired detection center frequency of 4.0 GHz. Each such waveguide 54a, 54b has one leg 56a which extends along the ridge and a second leg 56b which extends perpendicular to the ridge into the promontory 13. The two legs meet at a meeting wall 56c spaced a selected distance from the adjacent end of slot 16. Due to the presence of slot 16, each waveguide leg 56a is bifurcated at the slot, i.e. it includes two halves located on opposite sides of slot 16.

As best seen in FIGS. 3-5, when cartridge 14 is properly seated in housing 10 the two metallized notches 36 in support member 18 are located directly opposite the inner ends of the corresponding waveguide legs 56a so that the conductive upper and lower walls of each notch are essentially continuations or extensions of the upper and lower walls of the corresponding waveguide leg 56a, with the innermost wall of the notch helping to form the back plate for that leg, i.e. it fills in the space between the conductive inner ends of the waveguide leg 56a halves that are on opposite sides of slot 16 and completes the waveguide back plate.

On the other hand, the meeting wall 56c of each waveguide 54a, 54b is orientated at a 45° angle with respect to the ridge axis so that it constitutes an E-plane bend which redirects thermal radiation emanating from the adjacent leg of tube 20 and propagating along waveguide leg 56a vertically upwards into the corresponding waveguide leg 56b. In sum, the cartridge 14 structure and the ridge 52 structure combine and coact to provide the waveguides 54a and 54b that form the temperature sensing transducers $T_I$ and $T_O$, respectively, and lead the transducers outside heating cavity 12'. This mode of coupling to the outside is less lossy, less expensive and more forgiving than other coupling methods using coaxial connectors or probes, for example.

As best seen in FIGS. 3 and 5, each waveguide leg 56b leads to a waveguide-to-microstrip transition. Thus, for waveguide 54a there is a transition shown generally at 62a and for waveguide 54b there is a transition indicated generally at 62b. Preferably, the two transitions are mirror-images of one another and are part of a printed circuit board 64 that is mounted in housing 10, e.g. in promontory 13.

Circuit board 64 includes a substrate 66 and a printed circuit 68. Portions of substrate 66 extend into the waveguide legs 56b of each waveguide 54a, 54b. The substrate underside of each of those portions carries a microstrip 72 which projects into the associated waveguide leg 56b, being separated from the waveguide top wall 12a wall by an air gap 71 (FIG. 3) to form the transition 62a or 62b. These microstrips 72 are connected via plated through holes in substrate 66 to the remainder of the printed circuit 68 present on the upper surface of substrate 66 where the waveguide-generated outputs of the two transitions 62a and 62b are coupled by way of a switch 74 (SPST) to a radiometer 76 which may operate at a center frequency of 4.0 GHz. Both the switch and radiometer are controlled by the controller 33 which may be mounted on and connected to the printed circuit board 64. The switch and the radiometer preferably compromise a microwave integrated circuit (MIC) package which may be located directly above waveguide 12 close to the sensing transducers $T_I$ and as $T_O$, so as to minimize noise in the measured signal and to avoid the need for external cabling.

While the illustrated transitions 62a and 62b are microstrip transitions, other conventional transitions are possible such as a waveguide-to-stripline transition or a waveguide-to-coax-to-stripline transition.

When cartridge 14 is seated in housing 10 with fluid flowing through tube 20, that fluid will be warmed as it passes through the heating cavity 12' until the fluid reaches the temperature set by keypad 34. Since each sensing transducer $T_I$ or $T_O$ views only one leg of tube 20 terminated by the male connector 22b (FIG. 1) and provides a direct measurement of the temperature of the fluid in that leg, it is important that the cartridge 14 be oriented in housing 10 so that the outlet or exit leg 20b of tube 20 is the leg closer to the power source as shown in FIG. 3. To ensure this, the cartridge support member 18 may be provided with a polarity determination device, e.g. a longitudinal keyway 92 at one face thereof which is adapted to slidably receive a key 94 formed in the front edge of slot 16 as shown in FIG. 1. Then, when the cartridge bottoms in recess 42, the microswitch 46 will send an enabling signal to controller 33 indicating that the cartridge is properly seated in housing 10.

The apparatus may be turned on and off and be controlled via key pad 34 with the inlet and outlet temperatures being displayed in real time by display 35. The display may also display other parameters such as set point temperature, elapsed time, time of day, various diagnostics, etc.

The general operation of microwave warmers such as this is disclosed in my above patents.

When the apparatus 10 is in operation, the fluid flowing through the tube legs 20a and 20b in heating cavity 12' absorbs power and is heated as described above. The fluid in the tube segment 20c which is effectively outside the heating cavity is unaffected. The heat radiating from the fluid in the inlet leg 20a is sensed by transducer $T_I$ just as the fluid enters cavity 12' and a corresponding waveguide-generated signal is developed and applied via transition 62a and printed circuit 68 to switch 74. Similarly, thermal radiation heat from the fluid in the outlet leg 20b of tube 20 just as the fluid exits cavity 12' is sensed by transducer $T_O$ and a corresponding signal is applied via transition 62b to switch 74. Switch 74 may be toggled or switched by control signals from controller 33 to apply those waveguide-generated signals alternately to radiometer 76. As a result of this time sharing, the apparatus 10 requires only the one radiometer 76 that may be located inside the apparatus 10 right next to the transducers. The radiometer thereupon produces output signals accurately reflecting the fluid inlet and outlet temperatures. These signals may be applied by way of a conventional signal conditioning circuit 78 (filter, amplifier, A/D converter) to display 35 and also be used to control the transmitter as described in the above patents.

Since the transducers $T_I$ and $T_O$ sense the fluid right at the points where the fluid enters and leaves heating cavity 12', my apparatus also provides a very precise measurement of the flow rate through tube 20. More particularly, flow rate is determined by the following expression:

$$\frac{P(\text{watts})}{.07\Delta T(^\circ C.)} = \text{Flow Rate (ml/min.)}$$

where P=power absorbed (~equal to the applied power $P_0$), and
$\Delta T$=the difference between the fluid inlet and outlet temperatures.

Of course, this flow rate can also be displayed by display 35. This is an important feature because a nurse cannot measure flow rates greater than about 25 ml/min. by counting drips in the drip chamber of a fluid administration set because at that rate, the drips become a steady stream. The present apparatus can measure and display even such high flow rates using the above calculation.

It is important to note that when my apparatus is in operation, little or no radiation may leak from the heating cavity 12' through slot 16 at both the heating and detection frequencies. This is because, as noted above, the slot 16 is quite thin or narrow and the slot is effectively extended in length upward through the promontory 13. Also, the metallized side wall segments of support member 18 adjacent the tube legs extend a selected distance above heating cavity 12' as to create with the conductive walls of promontory 13 adjacent to those legs a length of dielectric-filled circular waveguide that is cut-off at both the heating and detection frequencies, thereby further isolating heating cavity 12'. As radiation leakage from slot 16 is minimized, so also is the coupling of external radiated interference into the apparatus 10 via slot 16 which could adversely affect the measured temperature. In other words, the promontory 13 and cartridge 14 structures at the mouth of slot 16 and the narrow slot itself combine and coact to create waveguide "chimneys" above heating cavity 12' which function as two-way filters to prevent radiation from entering or leaving the cavity. In addition, the promontory itself wraps around the cartridge to provide a guide for, and stabilizing influence on, the cartridge.

It will thus be seen that the objects set forth above, among those made apparent from the preceding description, are efficiently attained. Also, since certain changes may be made in the above construction without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention described herein.

What is claimed is:

1. Microwave warming apparatus comprising
a housing defining a heating waveguide having a pair of opposite electrically conductive end walls and electrically conductive longitudinal walls extending between the end walls, said walls enclosing a heating cavity;
an integral electrically conductive ridge projecting from one of the longitudinal walls and extending along the waveguide between the end walls;
a slot having opposite ends and extending from the outside through said one longitudinal wall and said ridge into the heating cavity, said slot being adapted to receive a cartridge containing a tube so that the tube extends through the slot into the heating cavity;
means for coupling electromagnetic energy having a selected heating frequency into the heating waveguide to heat the contents of the tube;
a first receiving waveguide extending inside said ridge adjacent to the slot so that when the cartridge is received in the slot, the first receiving waveguide can pick up thermal radiation emanating from a first segment of the tube and produce a corresponding waveguide-generated signal, and
a radiometer that operates at a selected detection frequency and is responsive to the waveguide-generated signal for producing a corresponding temperature signal.

2. The apparatus defined in claim 1 wherein the first receiving waveguide has an inner end located adjacent to the slot and extends along the ridge to a first transition located outside the heating cavity, said first transition being in circuit with the radiometer.

3. The apparatus defined in claim 2 wherein the first transition is a waveguide-to-strip-line transition.

4. The apparatus defined in claim 2 wherein the radiometer comprises a microwave integrated circuit (MIC).

5. The apparatus defined in claim 2
wherein the inner end of the first receiving waveguide is adjacent to one end of the slot, and
further including a second receiving waveguide extending inside the ridge and having an inner end located adjacent to the opposite end of the slot, said second receiving waveguide being similar to the first receiving waveguide and extending to a second transition located outside the heating cavity, said second transition being in circuit with the radiometer.

6. The apparatus defined in claim 5 and further including
a microwave integrated circuit (MIC) in the housing, said microwave integrated circuit including said radiometer, and a switch for connecting the first and second transitions alternately to the radiometer, and
a controller in the housing for switching the switch.

7. The apparatus defined in claim 5 wherein each of the first and second receiving waveguides includes a first leg which extends along the ridge to an E-Plane bend and a second leg which extends from said bend through said one longitudinal wall to the corresponding one of said transitions.

8. The apparatus defined in claim 7 wherein
said bend is a 45° bend, and
the first and second receiving waveguides are substantially filled with a dielectric material.

9. The apparatus defined in claim 5 and further comprising a cartridge received in said slot, said cartridge including
a tube loop having an inlet, an outlet and spaced-apart parallel coplanar legs connected by a connecting segment, said tube loop being shaped and dimensioned so that when the cartridge is received in the slot, one leg of the tube is adjacent to one end of the slot and the other leg of the tube is adjacent to the opposite end of the slot, both legs extending into the heating cavity, and
a flat, relatively rigid support member having upper and lower ends and spaced-apart parallel side walls secured to said legs to maintain the shape of the tube loop.

10. The apparatus defined in claim 9 and further including an interior recess in a longitudinal wall of the heating waveguide opposite the slot, said recess being dimensioned to receive said connecting segment so that the connecting segment is outside the heating cavity.

11. The apparatus defined in claim 9 wherein the tube legs are spaced apart a quarter wavelength or multiple thereof at said heating frequency.

12. The apparatus defined in claim 9 wherein
the opposite side walls of the support member have first and second notches located directly opposite said inner ends of the first and second receiving waveguides, respectively, and
said first and second notches have walls which are electrically conductive and together with the first and second receiving waveguides comprise first and second transducers, respectively.

13. The apparatus defined in claim 12 wherein
the spacing of the inner ends of the first and second receiving waveguides is less than the length of the slot so that each receiving waveguide has a segment which brackets the slot and extends to the corresponding notch in the cartridge so that the walls of each notch form part of the adjacent one of the first and second receiving waveguides.

14. The apparatus defined in claim 9 wherein
the housing includes an exterior promontory projecting from said one longitudinal wall, said promontory having electrically conductive surfaces bordering the opposite ends of said slot;
a segment of the support member above said heating cavity has conductive surfaces, and
the heights of the promontory and the support member are selected so that together they form circular waveguides around the tube loop legs above said heating cavity which function as two-way filters at said heating and detection frequencies to prevent passage of electromagnetic radiation through said slot.

15. The apparatus defined in claim 1 and further comprising a cartridge in the slot, said cartridge including
a tube having a first segment;
a support member having a wall supporting the tube so that said first tube segment extends through the slot and past the first receiving waveguide into the heating cavity, and
a notch in said wall adjacent to the first tube segment, said notch being located directly opposite an inner end of the first receiving waveguide and having electrically conductive walls, said walls and the first receiving waveguide constituting a first transducer.

16. The apparatus defined in claim 15 wherein the notch and said inner end of the first receiving waveguide constitute a first transducer which brackets the first tube segment.

17. The apparatus defined in claim 16
further including a second transducer at the opposite end of the slot, said second transducer being similar to said first transducer, and
wherein the tube includes a second segment which extends past the second transducer into the heating cavity.

18. The apparatus defined in claim 15 wherein
the housing has an electrically conductive exterior wall extending up from said one longitudinal wall adjacent to the first tube segment, and the support member includes an upper segment that extends above the slot opposite said exterior wall and has electrically conductive surfaces so that the upper segment and exterior wall together form a circular waveguide around the first tube segment above the slot that is tuned to function as a two-way filter at said heating and detection frequencies.

* * * * *